(12) United States Patent
Forsell

(10) Patent No.: US 10,667,894 B2
(45) Date of Patent: *Jun. 2, 2020

(54) ANAL INCONTINENCE DISEASE TREATMENT WITH CONTROLLED WIRELESS ENERGY SUPPLY

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 774 days.

This patent is subject to a terminal disclaimer.

(21) Appl. No.: 15/262,133

(22) Filed: Sep. 12, 2016

(65) Prior Publication Data
US 2017/0196670 A1 Jul. 13, 2017

Related U.S. Application Data

(63) Continuation of application No. 14/037,438, filed on Sep. 26, 2013, now Pat. No. 9,439,744, which is a continuation of application No. 12/656,513, filed on Feb. 1, 2010, now Pat. No. 8,545,384, which is a continuation of application No. 10/270,168, filed on Oct. 15, 2002, now Pat. No. 7,666,132, which is a continuation of application No. 09/502,091, filed on Feb. 10, 2000, now Pat. No. 6,471,635.

(60) Provisional application No. 60/148,345, filed on Aug. 12, 1999.

(51) Int. Cl.
*A61F 2/00* (2006.01)
*A61N 1/378* (2006.01)

(52) U.S. Cl.
CPC ............ *A61F 2/0009* (2013.01); *A61F 2/004* (2013.01); *A61F 2/0036* (2013.01); *A61N 1/3787* (2013.01)

(58) Field of Classification Search
CPC .............................. A61F 2/0018; A61F 2/0036
USPC .............. 600/29–32; 128/897, 898, DIG. 25
See application file for complete search history.

(56) References Cited

U.S. PATENT DOCUMENTS

| | | | | |
|---|---|---|---|---|
| 3,750,194 A * | 8/1973 | Summers | ................ | A61F 2/004 623/23.66 |
| 5,328,077 A * | 7/1994 | Lou | .................. | A61B 17/00234 227/107 |
| 5,522,788 A * | 6/1996 | Kuzmak | .......... | A61B 17/00234 600/141 |
| 6,074,341 A * | 6/2000 | Anderson | ............. | A61F 2/0036 128/DIG. 25 |
| 6,471,635 B1 * | 10/2002 | Forsell | ................. | A61F 2/0036 600/30 |

* cited by examiner

*Primary Examiner* — Samuel G Gilbert

(57) ABSTRACT

A anal incontinence disease treatment apparatus comprises an operable restriction device implanted in a patient and engaging the colon or engaging the rectum to form a restricted fecal passageway in the colon or the rectum. A source of energy external to the patient's body and a control device for releasing wireless energy from the source of energy from outside the patient's body are provided, wherein the released wireless energy is used in connection with the operation of the restriction device.

21 Claims, 7 Drawing Sheets

ANAL INCONTINENCE DISEASE TREATMENT WITH CONTROLLED WIRELESS ENERGY SUPPLY

BACKGROUND OF THE INVENTION

The present invention relates to an anal incontinence treatment apparatus. More specifically, the invention relates to an anal incontinence treatment apparatus for surgical application in the abdomen of a patient for forming a restricted fecal passgeway in the colon or rectum. The term "patient" includes an animal or a human being.

Anal incontinence is a wide-spread disease. Several kinds of sphincter plastic surgery are used today to remedy anal incontinence. There is a prior manually operated sphincter system in an initial clinical trial phase where a hydraulic sphincter system connected to an elastic reservoir (balloon) placed in the scrotum is developed. A disadvantage of this system is that thick, hard fibrosis is created around the reservoir by pump movements making the system useless sooner or later.

U.S. Pat. No. 5,593,443 discloses a hydraulic anal sphincter under both reflex and voluntary control. A pressure controlled inflatable artificial sphincter is disclosed in U.S. Pat. No. 4,222,377.

SUMMARY OF THE INVENTION

The object of the present invention is to provide a new convenient anal incontinence treatment apparatus, the performance of which may be affected by the patient at any time after operation, in particular when need arise over the course of a day, so that the patient substantially always is satisfied or comfortable.

Accordingly, there is provided an anal incontinence disease treatment apparatus, comprising an operable restriction device implanted in a patient and engaging the colon or the rectum to form a restricted fecal passageway in the colon or rectum, a source of energy external to the patient's body, and a control device for releasing wireless energy from the external source of energy, wherein the released wireless energy is used in connection with the operation of the restriction device.

As a result, the advantage is achieved that the implanted restriction device can be non-invasively adjusted by the control device. Furthermore, the apparatus of the invention provides simple and effective control of the energy supplied to implanted components of the apparatus which ensures an extended and reliable functionality of the apparatus, possibly for the rest of the patient's natural life, and at lest many years.

The restriction device preferably controls the cross-sectional area of the fecal passageway in the colon or rectum, which gives the advantage that the patient is enabled to adjust the cross-sectional area of the fecal passageway whenever he likes during the day. This advantage should not be underestimated.

Preferably the control device also controls the restriction device. The control device may comprise an internal control unit, preferably including a microprocessor, implanted in the patient for controlling the restriction device. The control device may further comprise an external control unit outside the patient's body, wherein the internal control unit is programmable by the external control unit, for example for controlling the restriction device over time. Alternatively, the internal control unit may control the restriction device over time in accordance with an activity schedule program, which may be adapted to the patient's needs.

Conveniently, the external control unit may load the internal control unit with data in accordance with a loading mode only authorized for a doctor. For specialized controls of the restriction device, the external control unit may control the internal control unit in accordance with a doctor mode only authorized for the doctor. For simple controls of the restriction device, the external control unit may control the internal control unit in accordance with a patient mode permitted for the patient. Thus, by using the external control unit in accordance with different modes it is possible to have certains functions of the restriction device controlled by the patient and other more advanced functions controlled by the doctor, which enables a flexible post-operation treatment of the patient.

Generally, the apparatus further comprises an operation device implanted in the patient for operating the restriction device, wherein the control device controls the operation device to operate the restriction device.

The operation device may comprise hydraulic means and at least one valve for controlling a fluid flow in the hydraulic means. The control device may suitably comprise a wireless remote control for controlling the valve. The restriction device may comprise hydraulic means and the operation device may comprise a reservoir forming a fluid chamber with a variable volume connected to the hydraulic means. The operation device may distribute fluid from the chamber to the hydraulic means by reduction of the volume of the chamber and withdraw fluid from the hydraulic means to the chamber by expansion of the volume of the chamber.

In accordance with a first main aspect of the invention, the wireless energy is directly used for operation of the restriction device, i.e. the restriction device is operated as the wireless energy is released from the external source of energy by the control device. The term "directly" is used to mean, on one hand, that the restriction device is promptly operated by using the released energy without first storing the latter, on the other hand, that the released energy may be somewhat delayed, in the order of seconds, by for instance an energy stabilizer before being used for the operation of the restriction device. As a result, a very simple control of the restriction device is achieved and there are only a few implanted components of the apparatus. For example, there is no implanted source of energy, such as a battery, nor any implanted complicated signal control system. This gives the advantage that the apparatus will be extremely reliable.

The wireless energy may be used for direct operation of the restriction device in a non-magnetic and/or non-mechanical manner.

Generally, the control device controls and directly or indirectly powers the operation device with wireless energy released from the source of energy and/or powers other implanted energy consuming components of the apparatus.

In a first particular embodiment in accordance with the first main aspect of the invention, the operation device comprises a motor, preferably an electric motor which may have electrically conductive parts made of plastics. The motor may include a rotary motor, wherein the control device is adapted to control the rotary motor to rotate a desired number of revolutions. Alternatively, the motor may include a linear motor, or a hydraulic or pneumatic fluid motor, wherein the control device is adapted to control the fluid flow through the fluid motor. Motors currently available on the market are getting smaller and smaller. Furthermore, there is a great variety of control methods and miniaturized control equipment available. For example, a number of revolutions of a rotary motor may be analyzed by a Hall-element just a few mm in size.

In a second particular embodiment in accordance with the first main aspect of the invention, the control device is adapted to shift polarity of the polarized energy to reverse the operation device. The operation device may suitably comprise an electric motor and the released energy may comprise electric energy.

In a third particular embodiment in accordance with the first main aspect of the invention, the restriction device is operable to perform a reversible function. Such a reversing function preferably involves enlarging and restricting the fecal passageway by the restriction device, suitably in a stepless manner. There is a reversing device implanted in the patient for reversing the function performed by the restriction device. In this connection, the control device suitably controls the reversing device, which may include a switch, to reverse the function performed by the restriction device. The reversing device may comprise hydraulic means including a valve for shifting the flow direction of a fluid in the hydraulic means. Alternatively, the reversing device may comprise a mechanical reversing device, such as a switch or a gear box.

Where the reversing device comprises a switch the control device suitably controls the operation of the switch by shifting polarity of released energy supplied to the switch. The switch may comprise an electric switch and the source of energy may supply electric energy for the operation of the switch. The switch mentioned above may comprise an electronic switch or, where applicable, a mechanical switch.

In accordance with the third particular embodiment, the operation device preferably comprises a motor, wherein the reversing device reverses the motor.

In a fourth particular embodiment in accordance with the first main aspect of the invention, the restriction device comprises hydraulic means, for example including an expansible/contractible cavity for fluid. The operation device preferably comprises a pump for pumping a fluid in the hydraulic means, a motor for driving the pump, a valveless fluid conduit between the pump and the hydraulic means of the restriction device, and a reservoir for fluid, wherein the reservoir forms part of the conduit. All of the hydraulic components involved are preferably devoid of any non-return valve. This is of great advantage, because with valves involved there is always a risk of malfunction due to inproperly working valves, especially when long time periods passes between valve operations. The reservoir may form a fluid chamber with a variable volume, and the pump may distribute fluid from the chamber to the hydraulic means of the restriction device by reduction of the volume of the chamber and withdraw fluid from the hydraulic means to the chamber by expansion of the volume of the chamber.

In accordance with a second main aspect of the invention, the apparatus comprises a switch implanted in the patient for directly or indirectly switching the operation of the restriction device and an internal source of energy, such as a battery, implanted in the patient for supplying energy for the operation of the restriction device, wherein the switch directly or indirectly affects the supply of energy from the internal source of energy. This solution is advantageous for embodiments of the apparatus that have a relatively high energy consumption which cannot be met by direct supply of wireless energy.

In a first particular embodiment in accordance with the second main aspect of the invention, the switch switches between an off mode, in which the internal source of energy is not in use, and an on mode, in which the internal source of energy supplies energy for the operation of the restriction device. In this case, the switch is conveniently operated by the wireless energy released from the external source of energy to switch between the on and off modes. The control device, preferably comprising a wireless remote control, may control the external source of energy to release the wireless energy. The advantage of this embodiment is that the lifetime of the implanted source of energy, such as a battery, can be significantly prolonged, since the implanted source of energy does not supply energy when the switch is in its off mode.

In a second particular embodiment in accordance with the second main aspect of the invention, the control device comprises a wireless remote control for controlling the internal source of energy. In this case, the switch is operable by the wireless energy from the external source of energy to switch between an off mode, in which the internal source of energy and remote control are not in use, and a standby mode, in which the remote control is permitted to control the internal source of energy to supply energy for the operation of the restriction device.

In a third particular embodiment in accordance with the second main aspect of the invention, the apparatus further comprises an energy transfer device implanted in the patient for transferring the wireless energy into storable energy, wherein the internal source of energy is capable of storing the storable energy. The internal source of energy preferably comprises an electric accumulator, at least one capacitor or at least one rechargeable battery, or a combination of at least one capacitor and at least one rechargeable battery. In this case, the switch switches from an off mode, in which the internal source of energy is not in use, to an on mode, in which the internal source of energy supplies energy for the operation of the restriction device.

The control device, preferably comprising a wireless remote control, may control the switch to switch between the on and off modes.

Alternatively, in this third particular embodiment an energy storage device may be implanted in the patient for storing the storable energy instead of the internal source of energy, wherein the switch is operable by energy from the implanted energy storage device to switch between an off mode, in which the internal source of energy is not in use, and an on mode, in which the internal source of energy supplies energy for the operation of the restriction device. In this case, the control device (the wireless remote control) controls the energy storage device to operate the switch.

The internal source of energy preferably comprises an electric source of energy, such as an accumulator or a battery having a life-time of at least 10 years. However, other kinds of sources are also conceivable, such as a nuclear source of energy or a chemical source of energy.

The above first, second and third and fourth particular embodiments described in connection with the first main aspect of the invention are also applicable in accordance with the second main aspect of the invention, i.e. where the apparatus comprises an implanted switch.

All of the above embodiments may be combined with at least one implanted sensor for sensing at least one physical parameter of the patient, wherein the control device may control the restriction device in response to signals from the sensor. For example, the sensor may comprise a pressure sensor for directly or indirectly sensing the pressure against the restriction device, human tissue or in the fecal passageway. The expression "indirectly sensing the pressure in the fecal passageway" should be understood to encompass the cases where the sensor senses the pressure against the restriction device or human tissue of the patient. The pressure sensor may be any suitable known or conventional pressure sensor such as shown in U.S. Pat. No. 5,540,731, 4,846,181, 4,738,267, 4,571,749, 4,407,296 or 3,939,823; or an NPC-102 Medical Angioplasty Sensor. Where the control device comprises an internal control unit implanted in the patient, the internal control unit may suitably directly control the restriction device in response to signals from the sensor. In response to signals from the sensor, for example pressure, the patient's position or any other important physical parameter, the internal control unit may send information thereon to outside the patient's body. The control unit may also automatically control the restriction device in response to signals from the sensor. The control device may control the restriction device in response to signals from the pressure sensor.

For example, the control unit may control the restriction device to further restrict the fecal passageway in the rectum in response to the sensor sensing that the patient is lying, or enlarge the fecal passageway in response to the sensor sensing an abnormally high pressure against the restriction device.

Where the control device comprises an external control unit outside the patient's body, the external control unit may, suitably directly, control the restriction device in response to signals by the sensor. The external control unit may store information on the physical parameter sensed by the sensor and may be manually operated to control the restriction device based on the stored information. In addition, there may be at least one implanted sender for sending information on the physical parameter sensed by the sensor.

An external data communicator may be provided outside the patient's body and an internal data communicator may be implanted in the patient for communicating with the external communicator. The implanted communicator may feed data related to the patient, or related to the implanted restriction device, back to the external communicator. Alternatively or in combination, the external communicator may feed data to the internal communicator. The implanted communicator may suitably feed data related to at least one physical signal of the patient.

Generally, the restriction device may control the cross-sectional area of the fecal passageway in the colon or rectum. For example, the restriction device may be operable to open and close the fecal passageway or may steplessly control the cross-sectional area of the fecal passageway. The restriction device may be non-inflatable, i.e. with no hydraulic fluid involved for the adjustments of the restriction device. This eliminates problems with fluid leaking from the restriction device.

The apparatus may comprise an implanted energy transfer device, wherein the control device releases electric energy and the energy transfer device transfers the electric energy into kinetic energy for, preferably direct, operation of the restriction device. Suitably, an implanted stabilizer, such as a capacitor or a rechargeable accumulator, or the like, may be provided for stabilizing the electric energy released by the control device.

The control device may release energy for a determined time period or in a determined number of energy pulses.

All of the above embodiments are preferably remote controlled. Thus, the control device advantageously comprises a wireless remote control transmitting at least one wireless control signal for controlling the restriction device. With such a remote control it will be possible to adapt the function of the apparatus to the patient's need in a daily basis, which is beneficial with respect to the treatment of the patient.

The wireless remote control may be capable of obtaining information on the condition of the implanted restriction device and of controlling the restriction device in response to the information. Also, The remote control may be capable of sending information related to the restriction device from inside the patient's body to the outside thereof.

In a particular embodiment of the invention, the wireless remote control comprises at least one external signal transmitter or tranceiver and at least one internal signal receiver or transceiver implanted in the patient. In another particular embodiment of the invention, the wireless remote control comprises at least one external signal receiver or transceiver and at least one internal signal transmitter or transceiver implanted in the patient.

The remote control may transmit a carrier signal for carrying the control signal, wherein the carrier signal is frequency, amplitude or frequency and amplitude modulated and is digital, analog or digital and analog. Also the control signal used with the carrier signal may be frequency, amplitude or frequency and amplitude modulated.

The control signal may comprise a wave signal, for example, a sound wave signal, such as an ultrasound wave signal, an electromagnetic wave signal, such as an infrared signal, a visible light signal, an ultra violet light signal, a laser signal, a micro wave signal, a radio wave signal, an x-ray radiation signal, or a gamma radiation signal. Where applicable, two or more of the above signals may be combined.

The control signal may be digital or analog, and may comprise an electric or magnetic field. Suitably, the wireless remote control may transmit an electromagnetic carrier wave signal for carrying the digital or analog control signal. For example, use of an analog carrier wave signal carrying a digital control signal would give safe communication. The control signal may be transmitted in pulses by the wireless remote control.

According to yet another aspect of the present invention there is provided a method of treating a human or animal having anal incontinence disease, comprising: (a) Surgically implanting in the human or animal an operable restriction device engaging the human's or animal's colon or rectum to form a restricted fecal passageway in the colon or rectum. (b) Providing a source of energy external to the patient's body. (c) Controlling the external source of energy from outside the patient's body to release wireless energy. And (d) using the released wireless energy in connection with the operation of the restriction device.

The method may further comprise (e) implanting in the human or animal an operation device which can adjust the restricted fecal passageway in response to supplied energy, and (f) using the released wireless energy to activate the implanted operation device so as (g) to enlarge the restricted fecal passageway to allow feaces to readily pass therethrough but normally restrict the fecal passageway.

In accordance with an alternative method, there is provided a method of treating a human or animal having anal incontinence disease, comprising the steps of placing at least two laparascopical trocars in the human's or animal's body, inserting a dissecting tool through the trocars and dissecting an area of the colon or rectum, placing an operable restriction device in the dissected area, so that the restriction device engages the colon or engages the rectum to form a restricted fecal passageway in the colon or rectum, providing a source of energy outside the human's or animal's body, controlling the external source of energy from outside the patient's body to release wireless energy, and using the released wireless energy in connection with the operation of the restriction device.

In accordance with another alternative method, there is provided a method of treating a human or animal having anal incontinence disease, comprising the steps of placing at least two laparascopical trocars in the human's or animal's body, inserting a dissecting tool through the trocars and dissecting an area of the colon or rectum, implanting an operable restriction device in the dissected area, so that the restriction device engages the colon or engages the rectum to form a restricted fecal passageway in the colon or rectum, implanting an energy transfer device, providing an external source of energy, controlling the external source of energy to release wireless energy, and transferring the wireless energy by the energy transfer device into energy different than the wireless energy for use in connection with the operation of the restriction device. This method may further comprise implanting a stabilizer in the human or animal for stabilizing the energy transferred by the energy transfer device.

It is the primary object of the present invention to provide a simple yet effective method and apparatus for treating chronic anal incontinence disease in humans or animals. This and other objects of the invention will become clear from an inspection of the detailed description of the invention and from the appended claims.

BRIEF DESCRIPTION OF THE DRAWINGS

Referring to the drawing figures, like reference numerals designate identical or corresponding elements throughout the several figures.

DETAILED DESCRIPTION OF THE DRAWINGS

Figure 1:
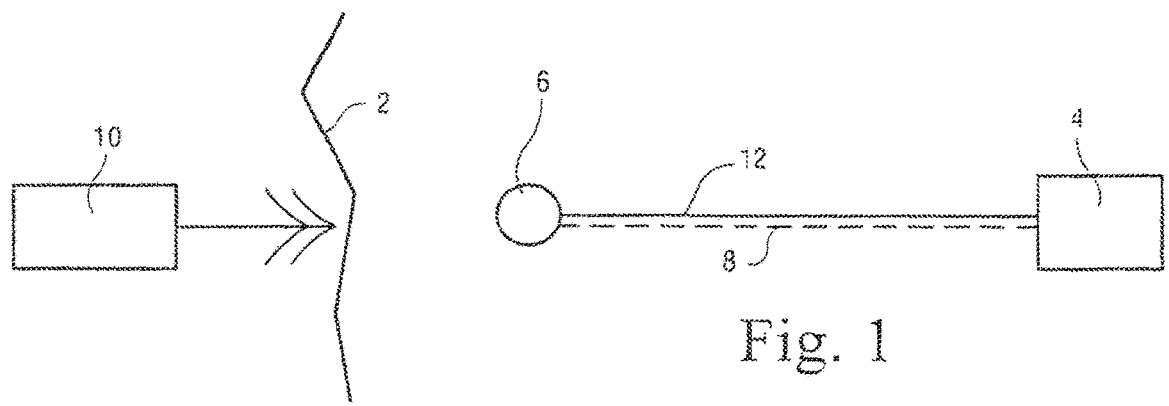
FIGS. 1 to 5 are schematic block diagrams illustrating five embodiments, respectively, of the invention, in which wireless energy released from an external source of energy is used for direct operation of a restriction device engaging the colon or rectum of a patient.

FIG. 1 schematically shows an embodiment of the anal incontinence disease apparatus of the invention having some parts implanted in a patient and other parts located outside the patient's body. Thus, in FIG. 1 all parts placed to the right of the patient's skin 2 are implanted and all parts placed to the left of the skin 2 are located outside the patient's body.

The apparatus of FIG. 1 comprises an implanted operable restriction device 4, which engages the patient's colon (or alternatively engages the rectum) to form a restricted fecal passageway in the colon or rectum. The restriction device 4 is capable of performing a reversible function, i.e. to enlarge and reduce the cross-sectional area of the fecal passageway, whereby the restriction device works as an artificial sphincter. An implanted control unit 6 controls the restriction device 4 via a control line 8 to form an adequate size of the cross-sectional area of the restricted fecal passageway. An external control unit 10 includes an external source of energy and a wireless remote control transmitting a control signal generated by the external source of energy. The control signal is received by a signal receiver incorporated in the implanted control unit 6, whereby the control unit 6 controls the implanted restriction device 4 in response to the control signal. The implanted control unit 6 also uses energy from the control signal for directly operating the restriction device 4 via a power supply line 12, as the control signal is transmitted.

Figure 2:
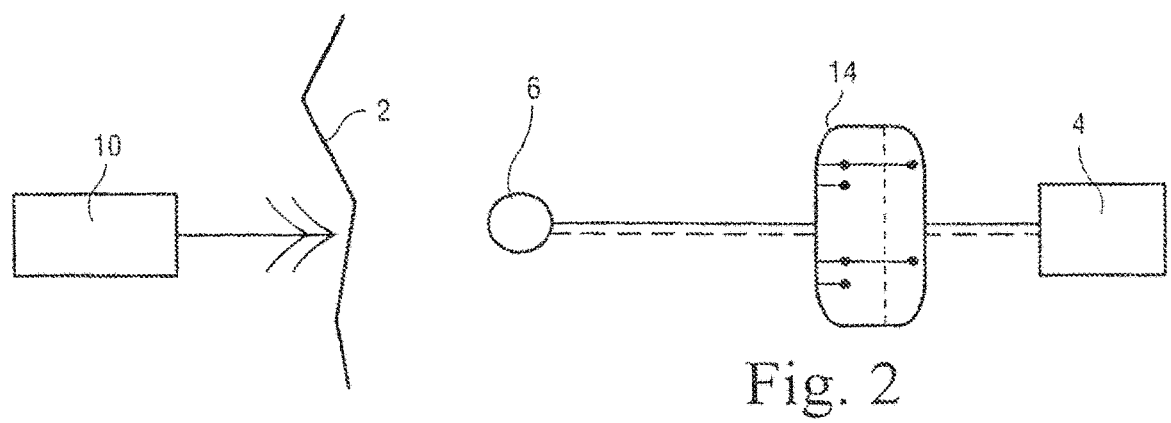

FIG. 2 shows an embodiment of the invention identical to that of FIG. 1, except that a reversing device in the form of a switch 14 also is implanted in the patient for reversing the restriction device 4. The control unit 6 uses the switch 14 to reverse the function performed by the restriction device 4, i.e. enlarging and restricting the fecal passageway. More precisely, the external control unit 10 releases energy carried by a wireless signal and the implanted control unit 6 transfers the wireless energy into a current for operating the switch 14. When the control unit 6 shifts the polarity of the current the switch 14 reverses the function performed by the restriction device 4.

Figure 3:
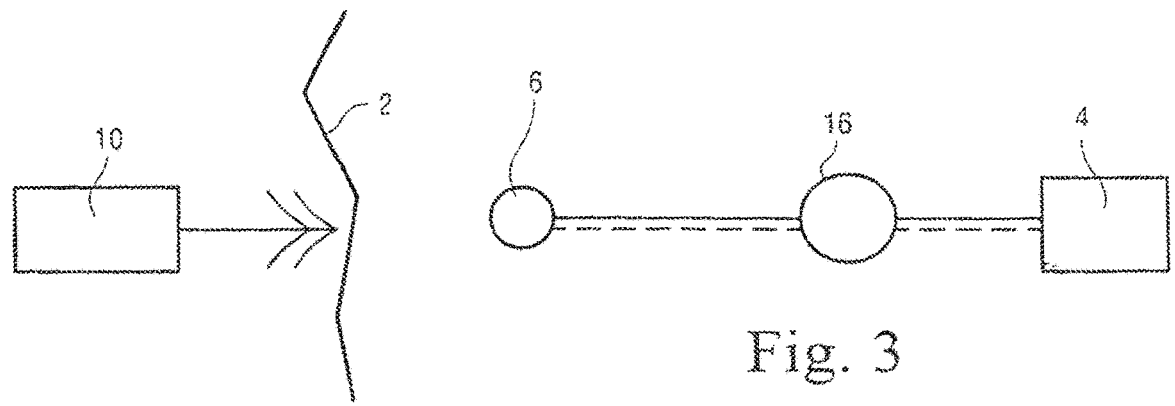

FIG. 3 shows an embodiment of the invention identical to that of FIG. 1, except that an operation device in the form of a motor 16 also is implanted in the patient. The implanted control unit 6 powers the motor 16 with wireless energy released from the external source of energy of the external control unit 10. The implanted control unit 6 controls the operation of the motor 16 in response to a control signal from the remote control of the external control unit 10.

Figure 4:
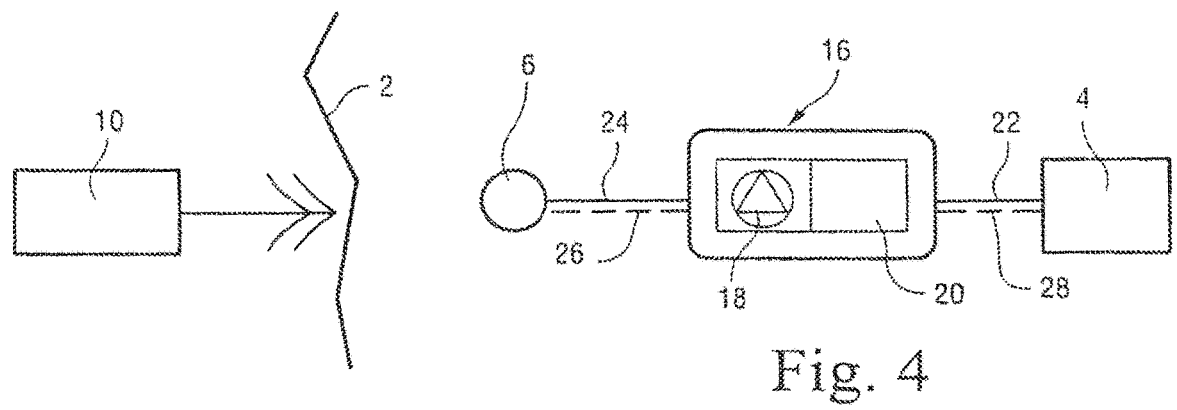

FIG. 4 shows an embodiment of the invention identical to that of FIG. 1, except that an assembly 16 including a motor/pump unit 18 and a fluid reservoir 20 also is implanted in the patient. In this case the restriction device 4 is hydraulically operated, i.e. hydraulic fluid is pumped by the motor/pump unit 18 from the reservoir 20 through a conduit 22 to the restriction device 4 to reduce the cross-sectional area of the fecal passageway, and hydraulic fluid is pumped by the motor/pump unit 18 back from the restriction device 4 to the reservoir 20 to enlarge the cross-sectional area. The external control unit 10 releases energy carried by a wireless signal and the implanted control unit 6 transfers the wireless energy into a current, for example a polarized current, for powering the motor/pump unit 18 via an electric power supply line 24. The implanted control unit 6 controls the motor/pump unit 16 and the restriction device 4 via control lines 26 and 28.

Figure 5:
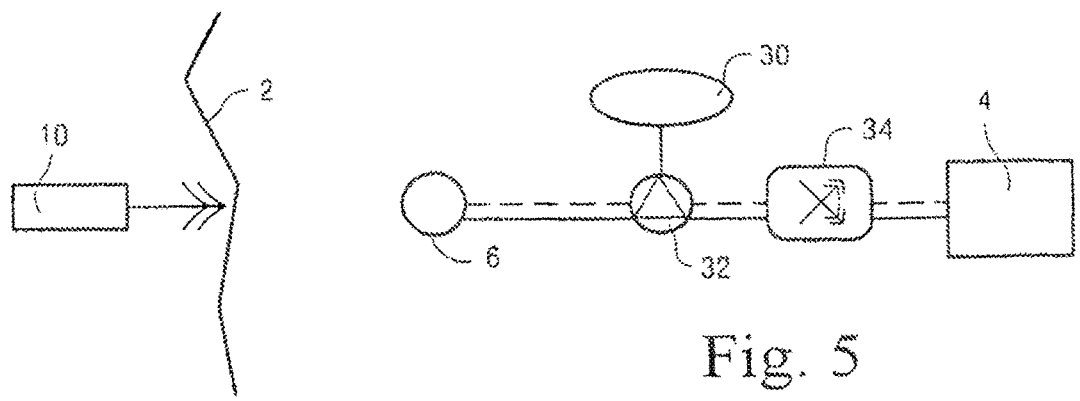

FIG. 5 shows an embodiment of the invention comprising the restriction device 4, hydraulically operated, and the implanted control unit 6, and further comprising a hydraulic fluid reservoir 30, a motor/pump unit 32 and a reversing device in the form of a hydraulic valve shifting device 34, all of which are implanted in the patient. The motor of the motor/pump unit 32 is an electric motor.

In response to a control signal from the wireless remote control of the external control unit 10 the implanted control unit 6 powers the motor/pump unit 32 with energy from the control signal, whereby the motor/pump unit 32 distributes hydraulic fluid between the reservoir 30 and the restriction device 4. The control unit 6 controls the shifting device 34 to shift the hydraulic fluid flow direction between one direction in which the fluid is pumped by the motor/pump unit 32 from the reservoir 30 to the restriction device 4 to reduce the cross-sectional area of the fecal passageway, and another opposite direction in which the fluid is pumped by the motor/pump unit 32 back from the restriction device 4 to the reservoir 30 to enlarge the cross-sectional area.

Figure 6:
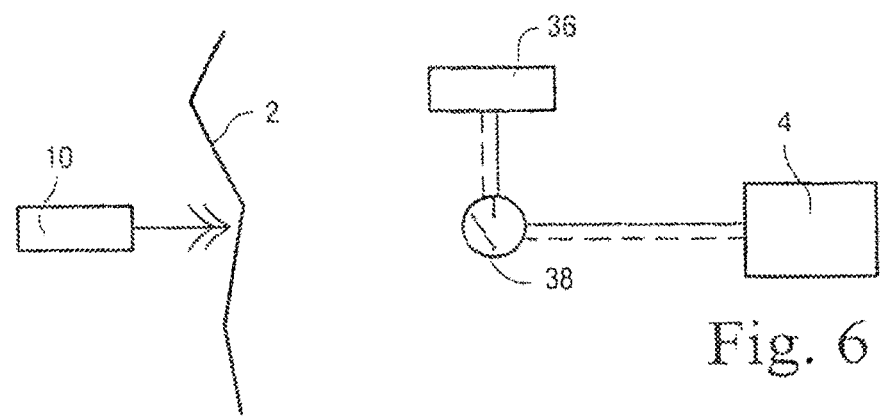
FIGS. 6 to 10 are schematic block diagrams illustrating five embodiments, respectively, of the invention, in which a switch is implanted in the patient for directly or indirectly switching the operation of the restriction device.

FIG. 6 shows an embodiment of the invention comprising the restriction device 4, the external control unit 10, an implanted source of energy 36 and an implanted switch 38. The switch 38 is operated by wireless energy released from the external source of energy of the external control unit 6 to switch between an off mode, in which the implanted source of energy 36 is not in use, and an on mode, in which the implanted source of energy 36 supplies energy for the operation of the restriction device 4.

Figure 7:
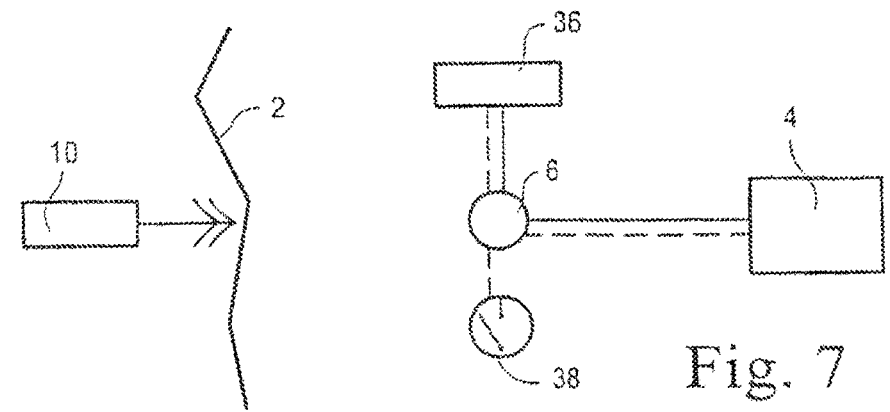

FIG. 7 shows an embodiment of the invention identical to that of FIG. 6, except that also the control unit 6 is implanted, in order to receive a control signal from the wireless remote control of the external control unit 10. The switch 38 is operated by the wireless energy from the external source of energy 10 to switch between an off mode, in which the implanted source of energy 36 and the wireless remote control of the external control unit 10 are not in use, i.e. the control unit 6 is not capable of receiving the control signal, and a standby mode, in which the wireless remote control is permitted to control the internal source of energy 36, via the implanted control unit 6, to supply energy for the operation of the restriction device 4.

Figure 8:
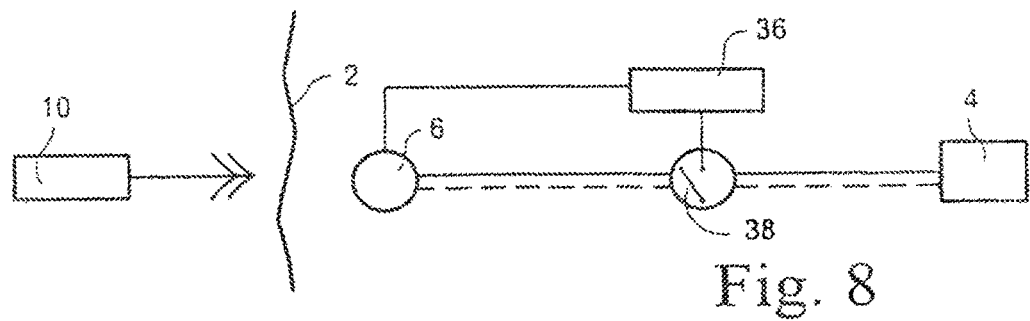

FIG. 8 shows an embodiment of the invention identical to that of FIG. 7, except that an energy transfer device for transferring the wireless energy into storable energy is incorporated in the implanted control unit 6 and that the implanted source of energy 36 is of a type that is capable of storing the storable energy. In this case, in response to a control signal from the external control unit 10, the implanted control unit 6 controls the switch 38 to switch from an off mode, in which the implanted source of energy 36 is not in use, to an on mode, in which the source of energy 36 supplies energy for the operation of the restriction device 4.

Figure 9:
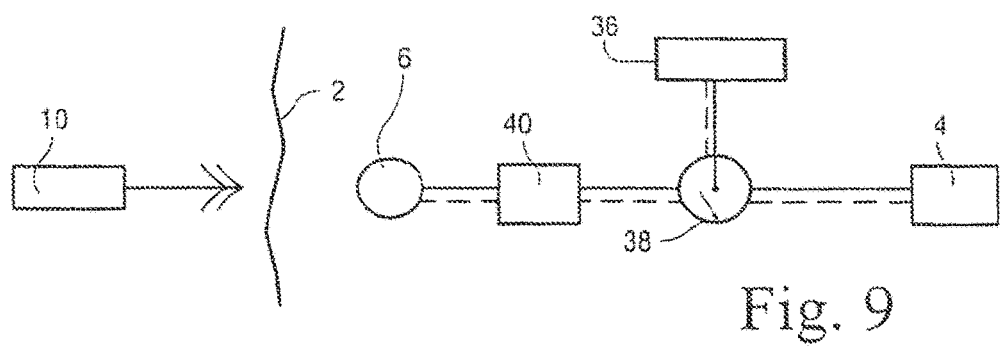

FIG. 9 shows an embodiment of the invention identical to that of FIG. 8, except that an energy storage device 40 also is implanted in the patient for storing the storable energy transferred from the wireless energy by the transfer device of the control unit 6. In this case, the implanted control unit 6 controls the energy storage device 40 to operate the switch 38 to switch between an off mode, in which the implanted source of energy 36 is not in use, and an on mode, in which the implanted source of energy 36 supplies energy for the operation of the restriction device 4.

Figure 10:
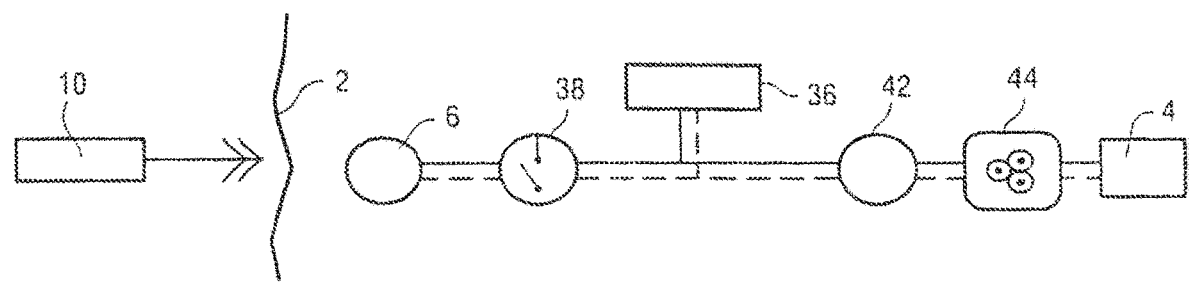

FIG. 10 shows an embodiment of the invention identical to that of FIG. 8, except that a motor 42 and a mechanical reversing device in the form of a gear box 44 also are implanted in the patient. The implanted control unit 6 controls the gear box 44 to reverse the function performed by the restriction device 4 (mechanically operated), i.e. enlarging and restricting the fecal passageway.

Figure 11:
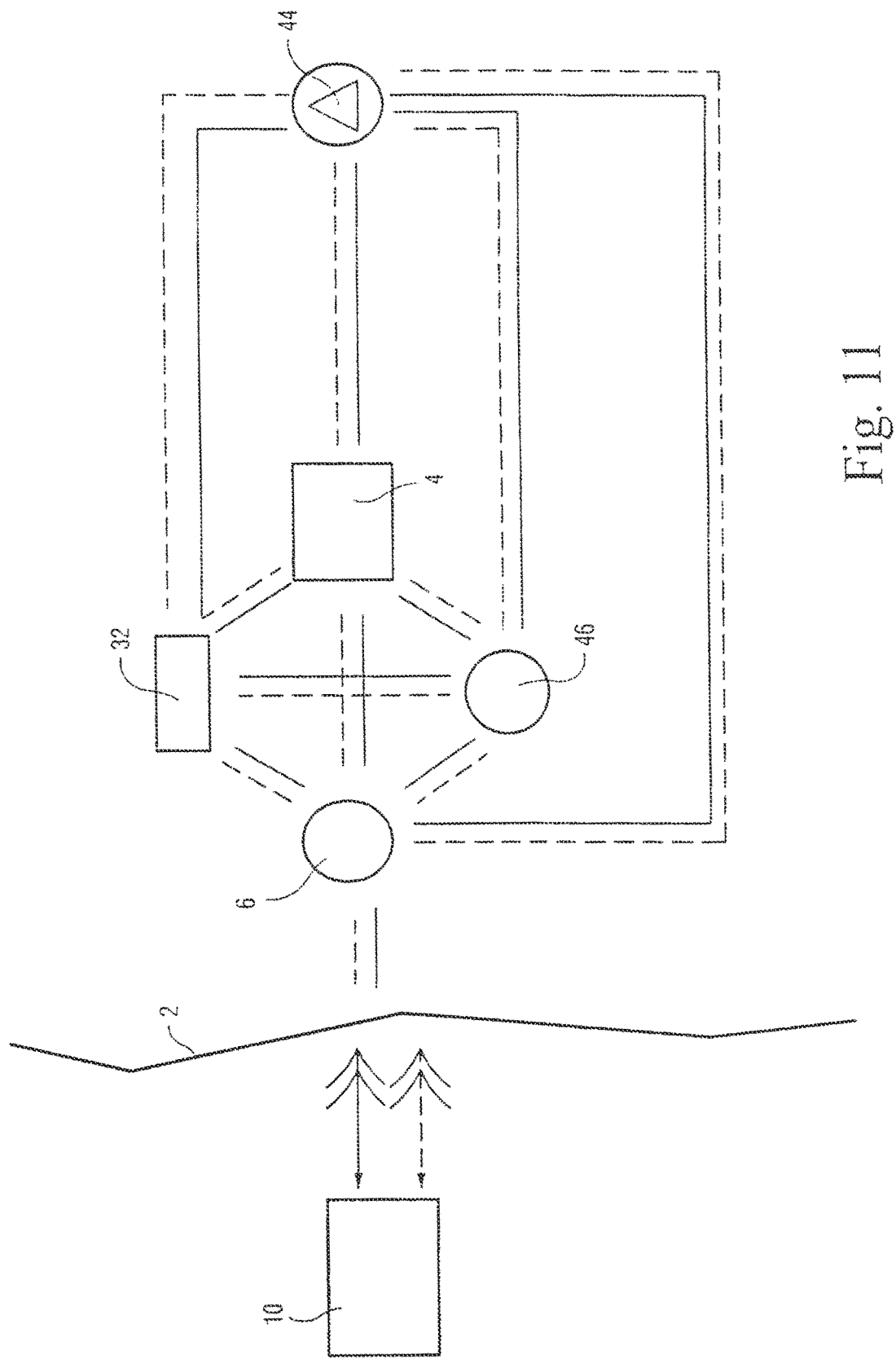
FIG. 11 is a schematic block diagram illustrating conceivable combinations of implanted components for achieving various communication options.

FIG. 11 schematically shows conceivable combinations of implanted components of the apparatus for achieving various communication options. Basically, there are the implanted restriction device 4, the implanted control unit 6 and the external control unit 10 including the external source of energy and the wireless remote control. As already described above the remote control transmits a control signal generated by the external source of energy, and the control signal is received by a signal receiver incorporated in the implanted control unit 6, whereby the control unit 6 controls the implanted restriction device 4 in response to the control signal.

A sensor 46 may be implanted in the patient for sensing a physical parameter of the patient, such as the pressure in the fecal passageway. The control unit 6, or alternatively the external control unit 10, may control the restriction device 4 in response to signals from the sensor 46. A tranceiver may be combined with the sensor 46 for sending information on the sensed physical parameter to the external control unit 10. The wireless remote control of the external control unit 10 may comprise a signal transmitter or tranceiver and the implanted control unit 6 may comprise a signal receiver or transceiver. Alternatively, the wireless remote control of the external control unit 10 may comprise a signal receiver or transceiver and the implanted control unit 6 may comprise a signal transmitter or transceiver. The above transceivers, transmitters and receivers may be used for sending information or data related to the restriction device 4 from inside the patient's body to the outside thereof.

Those skilled in the art will realize that the above various embodiments according to FIGS. 1-11 could be combined in many different ways.

Figure 12:
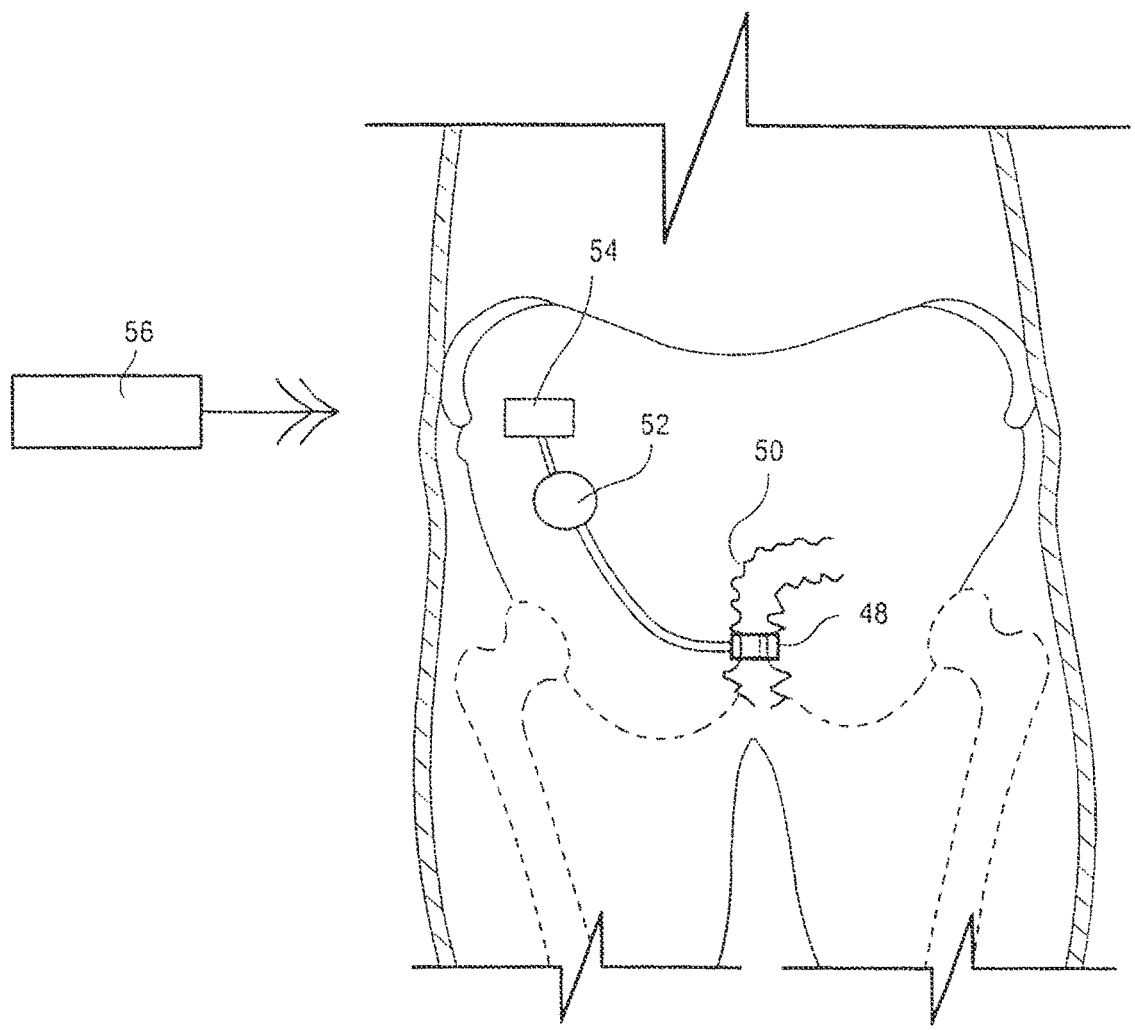
FIG. 12 illustrates the apparatus in accordance with the invention implanted in a patient.

FIG. 12 illustrates how any of the above-described embodiments of the anal incontinence disease treatment apparatus of the invention may be implanted in a patient. Thus, the apparatus comprises a restriction device 48 implanted in the patient and engaging the colon or rectum 50, and an operation device 52 for operating the restriction device 48. A control device in the form of a wireless remote control comprises an implanted control unit 54, which includes a signal receiver, for controlling the operation device 52, and an external control unit 56 including a signal transmitter for transmitting a control signal to the signal receiver of the implanted control unit 54. The implanted control unit 54 is capable of transferring signal energy from the control signal into electric energy for powering the operation device 52 and for energizing electric energy consuming implanted components of the apparatus.

Figure 13:
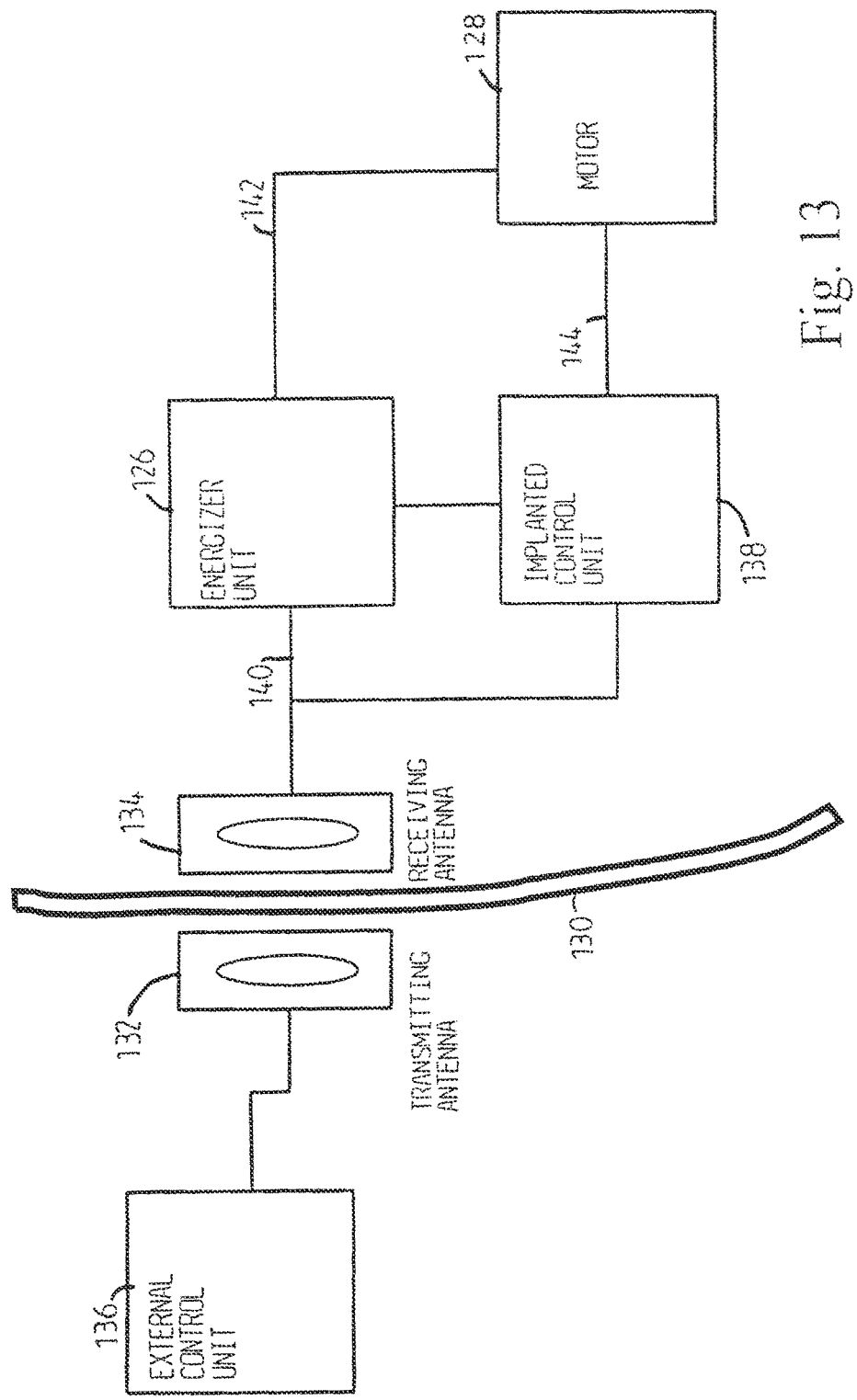
FIG. 13 is a block diagram illustrating remote control components of an embodiment of the invention.

FIG. 13 shows the basic parts of a wireless remote control of the apparatus of the invention including an electric motor 128 for operating a restriction device, for example of the type illustrated in FIG. 12. In this case, the wireless remote control is based on the transmission of electromagnetic wave signals, often of high frequencies in the order of 100 kHz-1 GHz, through the skin 130 of the patient. In FIG. 11, all parts placed to the left of the skin 130 are located outside the patient's body and all parts placed to the right of the skin 130 are implanted. Any suitable remote control system may be used.

An external signal transmitting antenna 132 is to be positioned close to a signal receiving antenna 134 implanted close to the skin 130. As an alternative, the receiving antenna 134 may be placed for example inside the abdomen of the patient. The receiving antenna 134 comprises a coil, approximately 1-100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The transmitting antenna 132 comprises a coil having about the same size as the coil of the receiving antenna 134 but wound with a thick wire that can handle the larger currents that is necessary. The coil of the transmitting antenna 132 is tuned to the same specific high frequency as the coil of the receiving antenna 134.

An external control unit 136 comprises a microprocessor, a high frequency electromagnetic wave signal generator and a power amplifier. The microprocessor of the control unit 136 is adapted to switch the generator on/off and to modulate signals generated by the generator to send digital information via the power amplifier and the antennas 132,134 to an implanted control unit 138. To avoid that accidental random high frequency fields trigger control commands, digital signal codes are used. A conventional keypad placed on the external control unit 136 is connected to the microprocessor thereof. The keypad is used to order the microprocessor to send digital signals to either contract or enlarge the restriction device. The microprocessor starts a command by applying a high frequency signal on the antenna 132. After a short time, when the signal has energized the implanted parts of the control system, commands are sent to contract or enlarge the restriction device in predefined steps. The commands are sent as digital packets in the form illustrated below.

| Start pattern, 8 bits | Command, 8 bits | Count, 8 bits | Checksum, 8 bits |
|---|---|---|---|

The commands are sent continuously during a rather long time period (e.g. about 30 seconds or more). When a new contract or enlarge step is desired the Count byte is increased by one to allow the implanted control unit 138 to decode and understand that another step is demanded by the external control unit 136. If any part of the digital packet is erroneous, its content is simply ignored.

Through a line 140, an implanted energizer unit 126 draws energy from the high frequency electromagnetic wave signals received by the receiving antenna 134. The energizer unit 126 stores the energy in a power supply, such as a large capacitor, powers the control unit 138 and powers the electric motor 128 via a line 142.

The control unit 138 comprises a demodulator and a microprocessor. The demodulator demodulates digital signals sent from the external control unit 136. The microprocessor of the control unit 138 receives the digital packet, decodes it and, provided that the power supply of the energizer unit 126 has sufficient energy stored, sends a signal via a signal line 144 to the motor 128 to either contract or enlarge the restriction device depending on the received command code.

Alternatively, the energy stored in the power supply of the energizer unit may only be used for powering a switch, and the energy for powering the motor 128 may be obtained from another implanted power source of relatively high capacity, for example a battery. In this case the switch is adapted to connect said battery to the control unit 138 in an Aon@ mode when said switch is powered by said power supply and to keep said battery disconnected from the control unit in a Astandby@ mode when said switch is unpowered.

Figure 14:
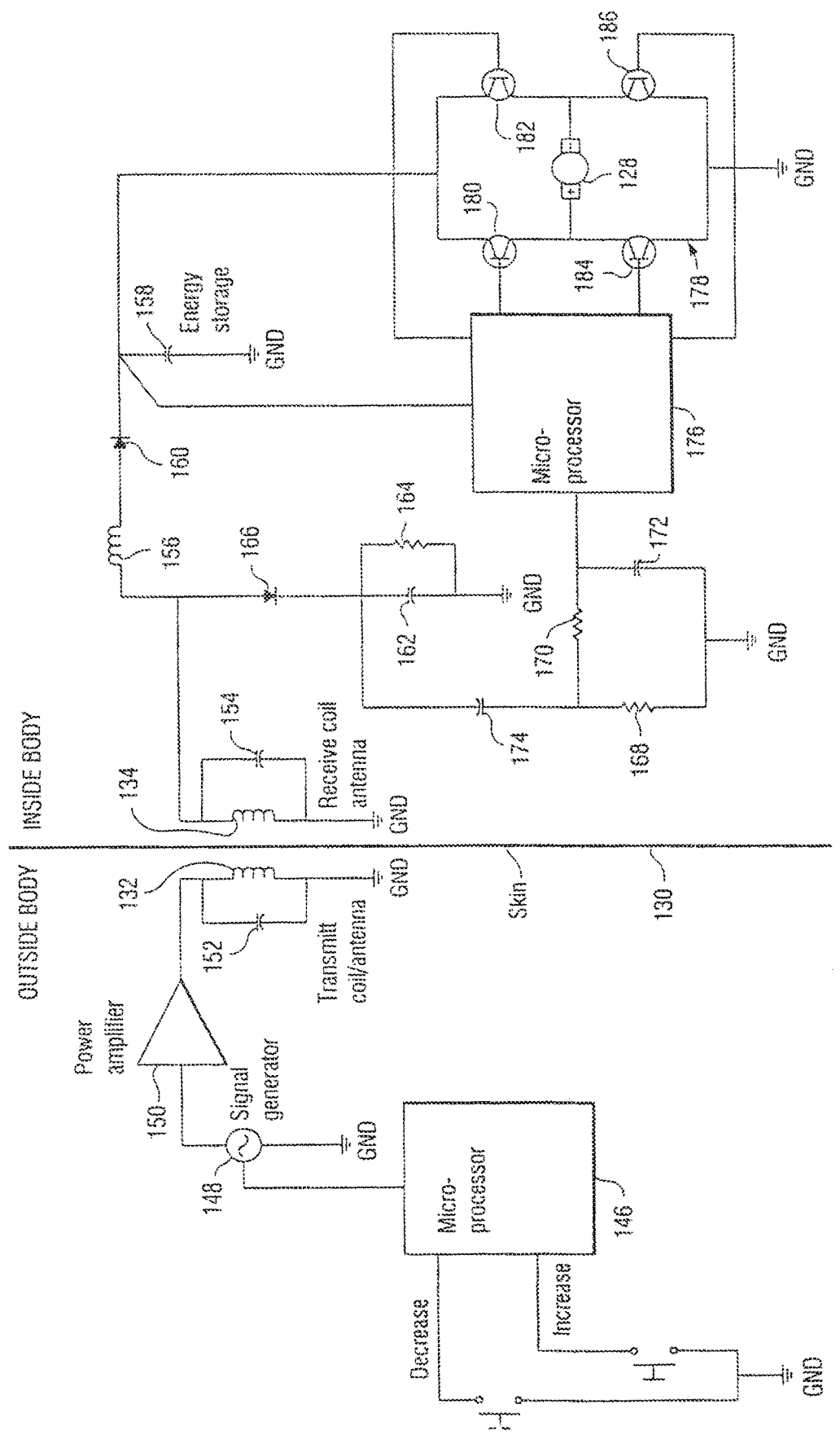
FIG. 14 is a schematic view of exemplary circuitry used for the components of the block diagram of FIG. 13.

With reference to FIG. 14, the remote control schematically described above will now be described in accordance with a more detailed embodiment. The external control unit 136 comprises a microprocessor 146, a signal generator 148 and a power amplifier 150 connected thereto. The microprocessor 146 is adapted to switch the signal generator 148 on/off and to modulate signals generated by the signal generator 148 with digital commands that are sent to implanted components of the apparatus. The power amplifier 150 amplifies the signals and sends them to the external signal transmitting antenna 132. The antenna 132 is connected in parallel with a capacitor 152 to form a resonant circuit tuned to the frequency generated by the signal generator 148.

The implanted signal receiving antenna coil 134 forms together with a capacitor 154 a resonant circuit that is tuned to the same frequency as the transmitting antenna 132. The signal receiving antenna coil 134 induces a current from the received high frequency electromagnetic waves and a rectifying diode 160 rectifies the induced current, which charges a storage capacitor 158. A coil 156 connected between the antenna coil 134 and the diode 160 prevents the capacitor 158 and the diode 160 from loading the circuit of the signal receiving antenna 134 at higher frequencies. Thus, the coil 156 makes it possible to charge the capacitor 158 and to transmit digital information using amplitude modulation.

A capacitor 162 and a resistor 164 connected in parallel and a diode 166 forms a detector used to detect amplitude modulated digital information. A filter circuit is formed by a resistor 168 connected in series with a resistor 170 connected in series with a capacitor 172 connected in series with the resistor 168 via ground, and a capacitor 174, one terminal of which is connected between the resistors 168, 170 and the other terminal of which is connected between the diode 166 and the circuit formed by the capacitor 162 and resistor 164. The filter circuit is used to filter out undesired low and high frequencies. The detected and filtered signals are fed to an implanted microprocessor 176 that decodes the digital information and controls the motor 128 via an H-bridge 178 comprising transistors 180,182,184 and 186. The motor 128 can be driven in two opposite directions by the H-bridge 178.

The microprocessor 176 also monitors the amount of stored energy in the storage capacitor 158. Before sending signals to activate the motor 128, the microprocessor 176 checks whether the energy stored in the storage capacitor 158 is enough. If the stored energy is not enough to perform the requested operation, the microprocessor 176 waits for the received signals to charge the storage capacitor 158 before activating the motor 128.

In the practice of the present invention the details of the elongated restriction device 4 (such as a gastric band) and the adjustment/operation device (which may have electric, hydraulic, or mechanical, etc. actuation) 6, may be as described in copending application Ser. No. 09/133,319, filed Aug. 13, 1998, Ser. No. 09/133,320, filed Aug. 13, 1998 and Ser. No. 09/133,322, filed Aug. 13, 1998, the disclosures of which are incorporated by reference herein.

The invention also comprises or consists of the foregoing structures and method steps, and is to be interpreted as broadly as allowed by the prior art.

What is claimed is:

1. A method for treating a patient suffering from anal incontinence by implanting an anal incontinence treatment apparatus, the method comprising the steps of:
   cutting the skin of the patient,
   inserting at least one dissecting tool,
   dissecting an area of a fecal passageway using said at least one dissecting tool,
   placing, in the patient, an operable restriction device adapted to be energized by a source of energy,
   placing the operable restriction device in the dissected area,
   forming a restricted fecal passageway, wherein the operable restriction device is adapted to change the opening of the fecal passageway, controlled from outside the patient's body,
   placing an internal data communicator adapted to communicate with an external data communicator intended to be placed outside the patient's body, and
   placing, in the patient, an energy transforming device adapted to transform wireless energy into an energy form different than the wireless energy used in connection with the operation of the restriction device.

2. The method according to claim 1, the method comprising the steps of:
enlarging the restricted fecal passageway to allow fecal matter to readily pass therethrough, and
restricting the fecal passageway, thereby
energizing the operable restriction device to open and close, respectively, the fecal passageway.

3. The method according to claim 1, the method comprising the steps of:
providing a source of energy external to the patient's body,
controlling the external source of energy from outside the patient's body,
releasing wireless energy and
using the released wireless energy in connection with the operation of the operable restriction device.

4. The method according to claim 1, wherein the method of implanting the anal incontinence treatment apparatus uses an implantable source of energy for the method step of:
placing, in the patient, an implantable source of energy, adapted to supply energy in connection with the operation of the restriction device.

5. The method according to claim 1, wherein the method of implanting the anal incontinence treatment apparatus uses an implantable stabilizer for the method step of:
placing, in the patient, the implantable stabilizer, adapted to be able to stabilize the energy transformed by the energy transforming device.

6. The method according to claim 1, wherein the operable restriction device comprises an electrically powered hydraulically operable restriction device, wherein the anal incontinence treatment apparatus comprises a reservoir and an operation device, wherein the step of placing the operable restriction device in the patient, further comprising the steps of:
placing, in the patient, the electrically powered hydraulically operable restriction device,
placing a reservoir adapted to contain hydraulic fluid,
placing an operation device, adapted to operate the hydraulically operable restriction device to move hydraulic fluid between the reservoir and the hydraulically operable restriction device and back, to restrict or release the hydraulically operable restriction device.

7. The method according to claim 6, further comprising:
operating from outside the patient's body the hydraulically operable restriction device, using the operation device and the hydraulic fluid of the reservoir, and
moving hydraulic fluid between the reservoir and the hydraulically operable restriction device and back, to restrict or release the hydraulically operable restriction device.

8. The method according to claim 1, wherein the method of implanting the anal incontinence treatment apparatus uses a control device comprising a second control unit for the method step of:
implanting, in the patient, the second control unit of the control device, adapted to control the operable restriction device in response to a signal received from a first control unit operable from outside the patient's body.

9. The method according to claim 8, comprising the method step of:
operating the first control unit of the control device from outside the patient's body for providing the signal,
controlling by the second implantable control unit of the control device the operable restriction device in response to the signal received from the first control unit, and
operating the operable restriction device, using the using the implantable second control unit of the control device.

10. The method according to claim 1, wherein the method of implanting an anal incontinence treatment apparatus uses electrical components comprising a stabilizer for the method step of:
placing, in the patient, the implantable stabilizer, adapted to be used when powering the operable restriction device.

11. The method according to claim 1, wherein the step of implanting the operable restriction device further comprises at least one of step a) and b);
a) implanting, in the patient, a motor adapted to operate the restriction device, or
b) implanting, in the patient, a pump adapted to operate the restriction device.

12. The method according to claim 1, wherein the method step of inserting at least one dissecting tool, further comprising the steps of:
inserting and placing at least two laparoscopic trocars in the patient's body,
inserting the at least one dissecting tool through at least one of the trocars, and
inserting a camera in another of the trocars, and
wherein the step of placing the operable restriction device in the patient, further comprising the steps of:
implanting, in the patient, the operation device and the gearbox, wherein the operation device comprises a motor, or a motor and a pump.

13. The method according to claim 1, wherein the method step of inserting at least one dissecting tool further comprises the steps of:
inserting and placing at least two laparascopic trocars in the patient's body,
inserting the at least one dissecting tool through at least one of the trocars, and
inserting a camera in another of the trocars, and wherein the method further comprising the steps of:
placing, in the patient, an implantable stabilizer adapted to be used when powering the operable restriction device.

14. The method according to claim 1, wherein the method step of inserting at least one dissecting tool, further comprising the steps of:
inserting and placing at least two laparascopic trocars in the patient's body,
inserting the at least one dissecting tool through at least one of the trocars,
inserting a camera in another of the trocars, and wherein the method further comprising the steps of:
implanting, in the patient, a receiving coil antenna comprising a resonant circuit comprising a capacitor and a coil for receiving transmitted wireless energy, wherein said resonant circuit is tuned to the same frequency as the transmitted wireless energy.

15. The method according to claim 14, further comprising:
operating, from outside the patient's body, the hydraulically operable restriction device, using the operation device and the hydraulic fluid of the reservoir, and moving hydraulic fluid between the reservoir and the hydraulically operable restriction device and back, to restrict or release the hydraulically operable restriction device.

16. The method according to claim 1, wherein the operable restriction device comprises an electrically powered hydraulically operable restriction device, wherein the anal incontinence treatment apparatus comprises a reservoir and an operation device, wherein the step of placing the operable restriction device in the patient, further comprising the steps of:
  placing, in the patient, the electrically powered hydraulically operable restriction device,
  placing a reservoir adapted to contain hydraulic fluid,
  placing an operation device, adapted to operate the hydraulically operable restriction device to move hydraulic fluid between the reservoir and the hydraulically operable restriction device and back, to restrict or release the hydraulically operable restriction device.

17. The method according to claim 1, wherein the method of implanting the anal incontinence treatment apparatus comprises the method steps of;
  providing an external source of energy,
  controlling the external source of energy to release wireless energy,
  transforming the wireless energy by the energy transforming device into an energy form different than the wireless energy, and
  using the different energy form in connection with the operation of the restriction device.

18. The method for treating a patient suffering from anal incontinence by implanting an anal incontinence treatment apparatus, the method comprising the steps of:
  cutting the skin of the patient,
  inserting at least one dissecting tool,
  dissecting an area of a fecal passageway using said at least one dissecting tool,
  placing, in the patient, an operable restriction device adapted to be energized by a source of energy,
  placing the operable restriction device in the dissected area, and
  forming a restricted fecal passageway, wherein the operable restriction device is adapted to change the opening of the fecal passageway, controlled from outside the patient's body, the method further comprising at least one of:
  implanting, in the patient, an operation device and a gearbox, wherein the operation device comprises a motor, or a motor and a pump;
  placing, in the patient, implantable electrical components, including placing, in the patient, at least one implantable voltage level guard, adapted to power the anal incontinence treatment apparatus; and
  implanting in the patient a receiving coil antenna comprising a resonant circuit comprising a capacitor and a coil for receiving transmitted wireless energy, wherein said resonant circuit is tuned to the same frequency as the transmitted wireless energy.

19. The method according to claim 18, wherein the method of implanting the anal incontinence treatment apparatus further comprises the method step of:
  operating the operable restriction device, using the operation device and the gearbox.

20. The method for treating a patient suffering from anal incontinence by implanting an anal incontinence treatment apparatus,
  the method comprising the steps of:
  cutting the skin of the patient,
  inserting at least one dissecting tool,
  dissecting an area of a fecal passageway using said at least one dissecting tool,
  placing, in the patient, an operable restriction device adapted to be energized by a source of energy,
  placing the operable restriction device in the dissected area, and
  forming a restricted fecal passageway, wherein the operable restriction device is adapted to change the opening of the fecal passageway, controlled from outside the patient's body, wherein the method step of inserting at least one dissecting tool, further comprising the steps of:
  inserting and placing at least two laparascopic trocars in the patient's body,
  inserting the at least one dissecting tool through at least one of the trocars, and
  inserting a camera in another of the trocars, and wherein the method further comprising the steps of:
  placing, in the patient, implantable electrical components, including
  placing, in the patient, at least one implantable voltage level guard adapted to power the anal incontinence treatment apparatus.

21. The method according to claim 20, comprising the method step of:
  operating the powered operable restriction device, using the at least one implantable voltage level guard.

* * * * *